United States Patent [19]
Thal

[11] Patent Number: 6,143,017
[45] Date of Patent: *Nov. 7, 2000

[54] FREE LOOP KNOTLESS SUTURE ANCHOR ASSEMBLY

[76] Inventor: Raymond Thal, 11321 Bright Pond La., Reston, Va. 22094

[ * ] Notice: This patent is subject to a terminal disclaimer.

[21] Appl. No.: 09/270,772

[22] Filed: Mar. 17, 1999

[51] Int. Cl.$^7$ .................................................. A61B 17/04
[52] U.S. Cl. .............................................................. 606/232
[58] Field of Search ........................... 606/282, 72, 73, 606/74, 75, 219, 224

[56] References Cited

U.S. PATENT DOCUMENTS

| | | |
|---|---|---|
| 4,007,743 | 2/1977 | Blake . |
| 4,532,926 | 8/1985 | O'Holla . |
| 4,632,101 | 12/1986 | Freedland . |
| 4,721,103 | 1/1988 | Freedland . |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. . |
| 5,141,520 | 8/1992 | Goble et al. . |
| 5,192,303 | 3/1993 | Gatturna et al. . |
| 5,207,679 | 5/1993 | Li . |
| 5,224,946 | 7/1993 | Hayhurst et al. . |
| 5,236,445 | 8/1993 | Hayhurst et al. . |
| 5,370,662 | 12/1994 | Stone et al. . |
| 5,569,306 | 10/1996 | Thal . |
| 5,658,313 | 8/1997 | Thal . |
| 5,665,112 | 9/1997 | Thal . |
| 5,683,419 | 11/1997 | Thal . |
| 5,709,708 | 1/1998 | Thal .................................. 606/232 |
| 5,720,765 | 2/1998 | Thal . |
| 5,728,136 | 3/1998 | Thal . |

*Primary Examiner*—Michael Buiz
*Assistant Examiner*—(Jackie) Tan Uyen T. Ho
*Attorney, Agent, or Firm*—Hoffman, Wasson & Gitler

[57] ABSTRACT

A free loop knotless suture anchor assembly for attachment of tissue to bone mass. The assembly includes a continuous suture loop and an anchor means for capturing portions of the loop with a snag means or recess thereon or therein the anchor means. Once the loop is captured, the anchor is inserted securely into a bone mass which facilitates in a repair of the torn away soft tissue.

6 Claims, 4 Drawing Sheets

FREE LOOP KNOTLESS SUTURE ANCHOR ASSEMBLY

BACKGROUND OF THE INVENTION

1. Field of the Invention

The present invention relates to a process and device or assembly for use in tissue repair. More particularly, there is provided an enhanced assembly that enables the attachment together or repair of portions of biological tissue, such as tendons or ligaments, on a bone surface. Such device or assembly is used in an unique way with novel components to reattach or attach tissue to bone.

2. Description of the Background Art

Soft tissues, such as tendons and ligaments, generally are attached to bone by small collagenous fibers. These connections are strong but permit the tendons and ligaments to be flexible. When a tissue, or a portion of a tissue, is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunneling techniques. These attachment devices are usually inserted through extensive surgical incisions and, in some circumstances, by arthroscopic surgical techniques. The use of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique free loop knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as prostheses, to bone. A suture anchor assembly is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

The applicant has developed a number of mechanisms for a tissue to bone repair which are disclosed in U.S. Pat. Nos. 5,569,306; 5,683,419; 5,728,136; 5,665,112; 5,658,313; 5,720,765; and 5,709,708.

It is an object of the present invention to provide a knotless suture anchor assembly which is easy to use and install.

Another object of the present invention is to provide a free loop suture anchor assembly which allows for secure attachment of soft tissue to a bone mass without the use or requirement of tying a knot during the surgical procedure.

Still another object of the present invention is to provide a suture anchor assembly which is compact and allows a surgeon to easily guide the anchor means into the bone mass, or an anchoring sleeve if desired, to enhance the security of the repair.

Yet another object of the present invention is to provide a process whereby a plurality of free loop knotless suture anchor assemblies can be used to effectively attach or reattach tissue to bone.

Further, another object of the present invention is a mechanism for producing incisions or cuts in tissue for performing reattachment or attachment of tissue to bone using the novel anchor assemblies.

A primary feature of the present invention is to provide free loop knotless anchor assembly that includes an unique snag-type or capture means on an anchoring means which facilitates engagement of the anchor means with the free continuous suture loop, for drawing soft tissue to the bone mass.

SUMMARY OF THE INVENTION

In accordance with the above objects, the present invention is directed to an assembly and a process of using at least one knotless suture anchor assembly for attachment or reattachment of biological soft tissue to bone. The unique enhanced free loop knotless suture anchor assembly may include one or a plurality of anchor means which can either be installed into a bone mass or into a hollow anchoring sleeve which has been installed into a bone mass. The hollow anchoring sleeve or anchor means can have varying shapes or surfaced exteriors for secure capturing or engagement with a bone mass. Each anchor means engages a free standing suture loop.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying structures which may embody the anchor means or the exterior of the anchoring sleeve of the invention.

Further, if desired, the hollow anchoring sleeve can contain a collar on the rear section or rear side to control the depth of sleeve insertion into the bone and prevent excessive insertion depth. The anchor means of the assembly has a first end or configuration which allows for secure capturing of either the hollow anchoring sleeve or the bone mass and a snag component for securing the free standing loop suture element. The first end of the anchor can be pointed or frustoconical in shape. The anchor means can be ribbed, beaded, threaded, or expandable on its exterior surface or further can contain one or more prongs for secure mating with the anchoring sleeve or bone mass.

The anchor means has located thereon or therein unique snag means in the shape of a hook, or other type projection, or a recess cut into the anchor means, or a slit cut into an existing opening in the anchor, for engaging the free standing continuous loop of a suture element. One particular embodiment provides a recess at the apex of the anchor whereby the free loop suture element can be snagged or captured by the anchor.

The free standing loop suture element can be a single continuous loop configuration or a plurality of suture lengths tied or attached to form a loop by any suitable means. A hook portion or projection of the anchor means can be made of the same material as the entire anchor means or a different material, as desired. The anchor assembly can be inserted during an open procedure, or an endoscopic procedure. In a preferred method, a first portion of the free standing loop suture element is passed through the soft tissue. The second portion is held for alignment. The two portions are then aligned and captured by the snag means of the anchor. The anchor means is then inserted into the bone mass or into a hollowing anchoring sleeve which has been inserted into the bone mass.

If desired, an user can use a plurality of assemblies to effectuate a repair.

The incisions, cuts or passages in the tissue can be accomplished by using needle and suture loop attachment assemblies which have been added to the free standing loop suture element. Upon capture of the first and second portions of the free standing loop suture element and after inserting same into bone mass, the needle and suture loop attachment assemblies are cut away and discarded. This assembly facilitates the method of stitching and reattachment.

Numerous other features of various embodiments of the enhanced knotless suture anchor assembly will be apparent from the following detailed description and the accompanying drawings.

DETAILED DESCRIPTION OF THE PRESENT INVENTION

Figure 1:
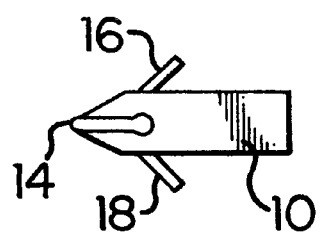
FIG. 1 is a perspective view of an anchor means having a depression or snag recess.
Figure 2:
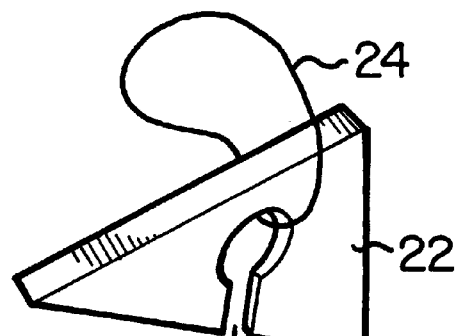
FIG. 2 is a perspective view of a wedge-type anchor means having a recess snag means with a continuous loop suture element.
Figure 3:
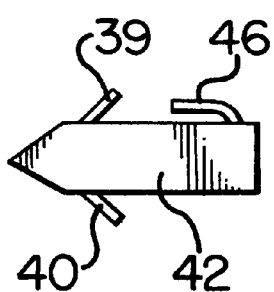
FIG. 3 is an alternate embodiment of an anchor means having a snag element.

Referring to FIGS. 1, 2 and 3, there is depicted three embodiments of anchor means containing snag recesses or snag means for capturing a free loop suture element. More particularly, FIG. 1 illustrates an anchor means 10 having prongs 16 and 18 which facilitate the attachment of the anchor means 10 to a bone mass. Provided in the body of the anchor means is a snag recess 14 for capturing a free loop suture element. The device can also contain, or be configured, with umbrella spokes or any other type of engaging features on its exterior for securing an attachment with a bone mass. All of these exterior attachment features are known to the industry and incorporated herein by reference.

FIG. 2 illustrates an alternate embodiment of the anchor means. Depicted is a wedge-like anchor means 22, a free loop suture element 24 and a snag means 26.

Figure 4:
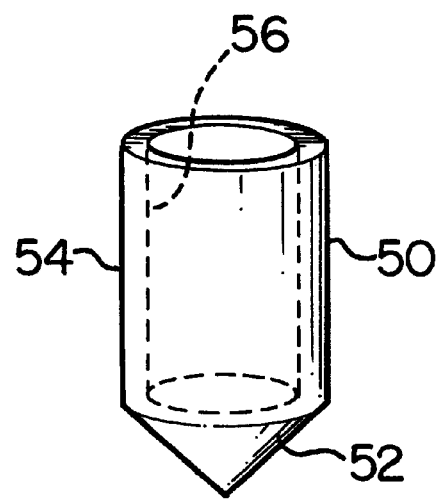
FIG. 4 is a depiction of a hollow anchoring means.
Figure 5:
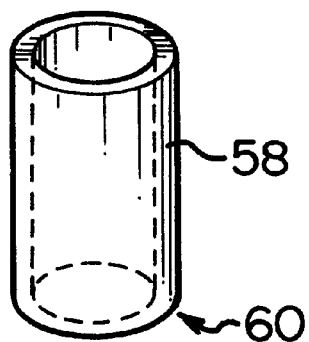
FIG. 5 is a depiction of an alternate embodiment of a hollow anchoring means.
Figure 6:
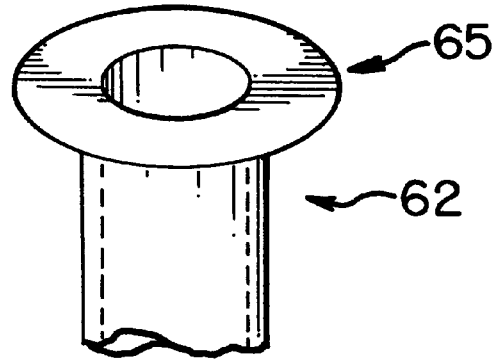
FIG. 6 is a depiction of an alternate embodiment of an anchoring means having a collar.

FIG. 3 illustrates another alternate embodiment of the present invention. Depicted is an anchor means 42, a snag means 46 located at a rear portion of the anchor means 42. Also pictured in this embodiment are two prongs 39 and 40 for secure attachment or mating with a bone mass or a hollow anchor assembly. FIGS. 4–6 depict three potential structures for a hollow anchoring means which can be utilized in conjunction with an anchor means for the desired repair. FIG. 4 depicts a hollow anchoring means 50 which has a pointed end for secure attachment to a bone mass. The exterior of the hollow anchoring means 54 may be smooth, or may contain a rough exterior for gripping a bone mass. In addition, any type of secure attachment means may be placed on the exterior 54 of the hollow anchoring means 50 for a secure attachment. Likewise, on the interior surface 56 such may be smooth or may be roughed or may contain any type of material or surfacing or means for securing gripping of an anchor means which is placed therein.

FIG. 5 depicts an alternate embodiment of a hollow anchoring means 58. The anchoring means 58 has a flat or rounded bottom end 60 and can be used for desired procedures. As is stated above, the exterior and interiors can be the same as that of the first embodiment.

Further, there is depicted an alternate embodiment of the top portion of a hollow anchor means 62. The top portion of any embodiment of the hollow anchoring means may contain a lip 65 which grips the surface of a bone mass once the hollow anchoring means is placed into a pre-drilled hole in a bone mass.

Figure 7:
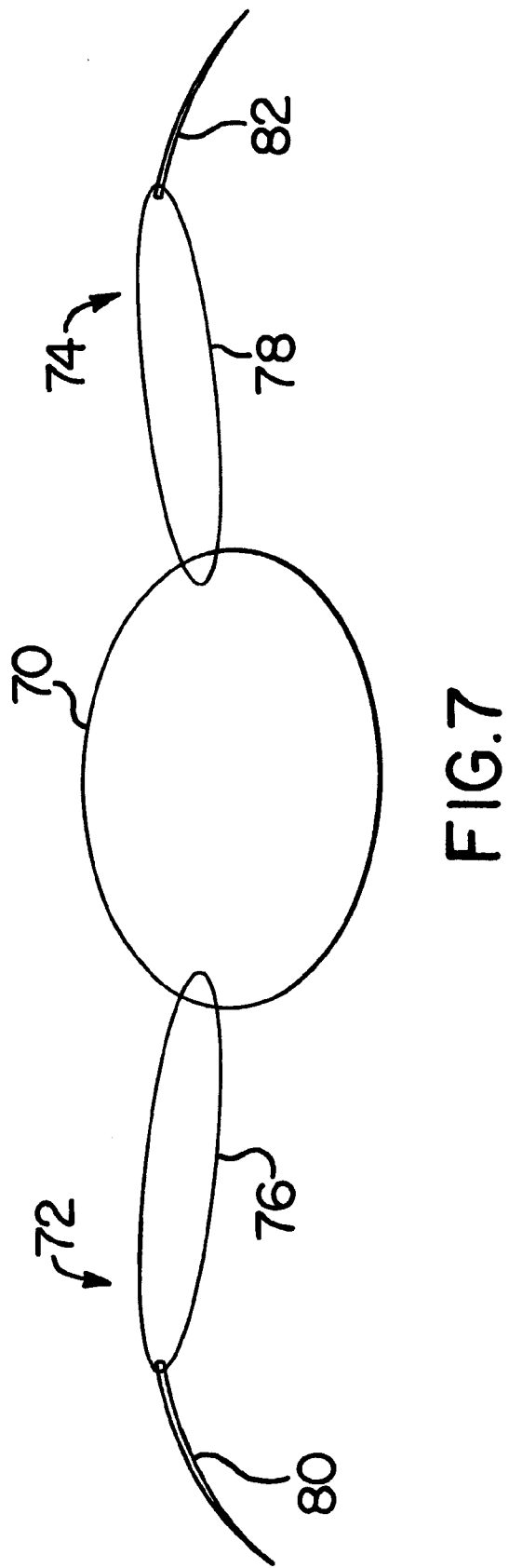
FIG. 7 is a depiction of a free loop suture element along with two needle cutaway suture piercing means.

FIG. 7 illustrates a free standing suture loop element 70 which is one continuous loop or a plurality of suture elements which have been tied together to form a continuous loop. Provided along with the free standing suture loop element are two needle suture breakaway elements 72 and 74, respectively. Each breakaway element is comprised of a suture loop 76 or 78, and a needle 80 or 82. The breakaway elements are used to pierce tissue and draw the free standing suture loop element therethrough during the attachment or reattachment procedure.

FIGS. 8, 9, 10 and 11 depict a method for reattaching or attaching tissue to bone using an embodiment of the invention.

Figure 8:
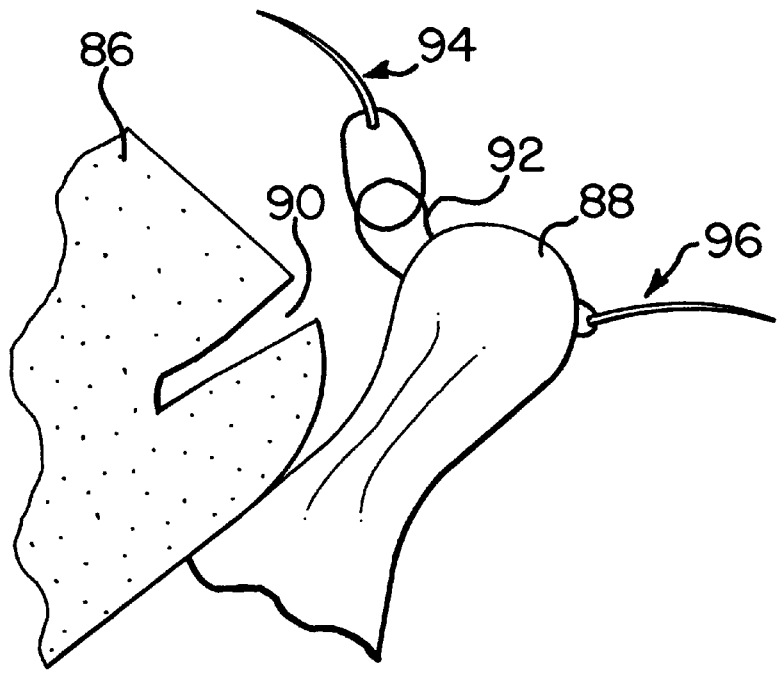
FIG. 8 illustrates a step in the procedure for attachment of tissue to bone mass utilizing components depicted in FIGS. 1 and 7.

In FIG. 8, there is depicted a bone mass 86 and a tissue element 88. Also illustrated is a pre-drilled hole 90 and a free standing suture loop element 92 which will facilitate the repair. Also depicted are needle suture breakaway elements 94 and 96 which are utilized during a repair procedure. Breakaway element 96 is pulled through tissue 88 in a first step of the repair.

Figure 9:
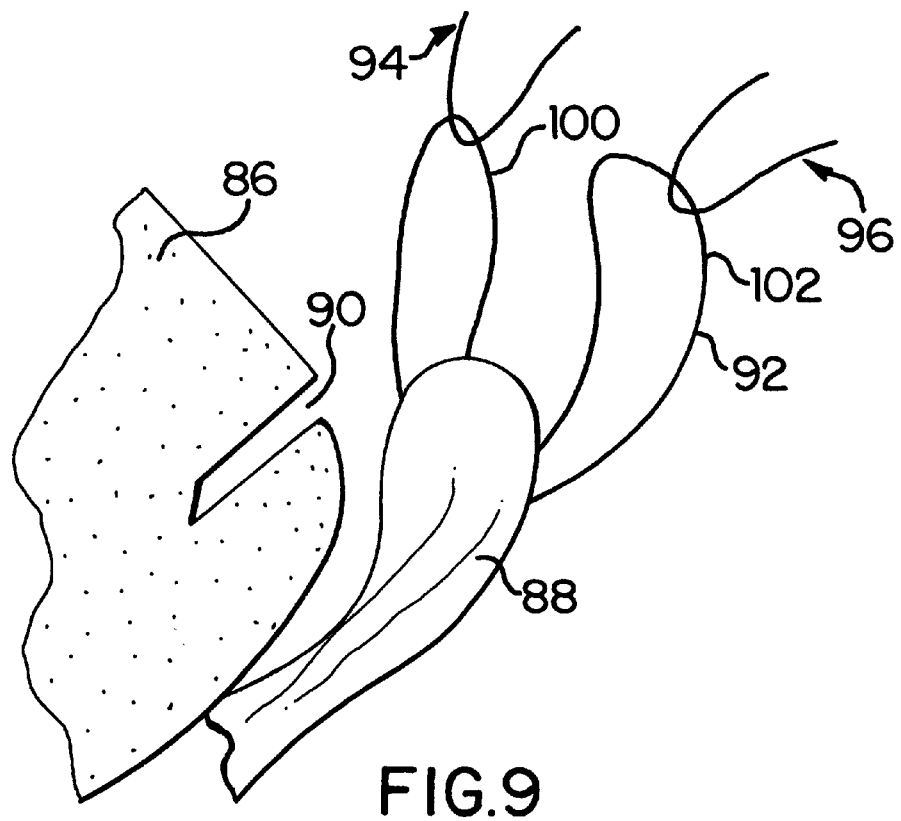
FIG. 9 illustrates a step in the procedure for attachment of tissue to bone mass.

In FIG. 9, the repair continues and free-standing suture loop element 92 is pulled further through tissue 88 until two loop sections 100 and 102 are brought into alignment.

Figure 10:
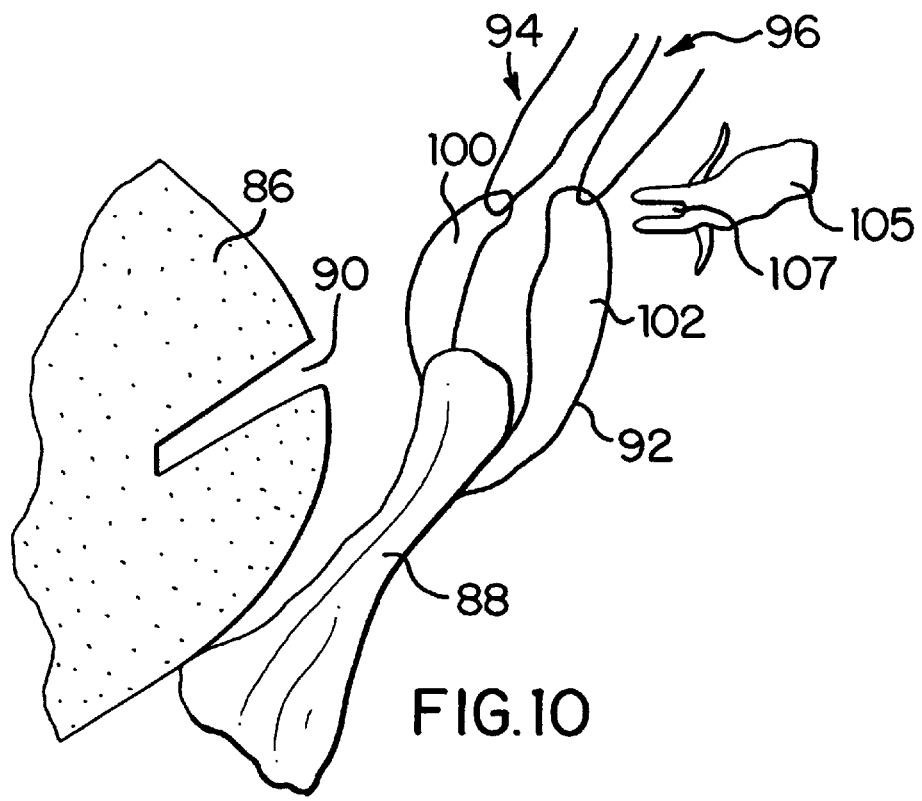
FIG. 10 illustrates a step in the procedure for attachment of tissue to bone mass.

In FIG. 10, an anchor means 105 is introduced which will engage free standing suture loop element 92, and more particularly, will snag in the snag means 107, the free aligned loop sections 100 and 102.

Figure 11:
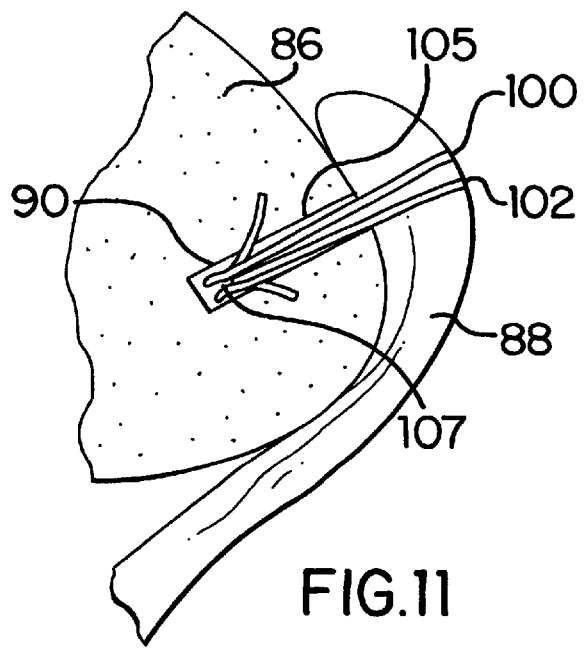
FIG. 11 illustrates the procedure showing attachment of tissue to bone mass embodying a method of the present invention.

FIG. 11 depicts a completed repair wherein tissue 88 has been attached to bone mass 86 in a secure fashion. Loop sections 100 and 102 of free standing suture loop element 92 have been captured by anchor means 105 in its snag recess 107 and drawn into the hole 90 in bone mass 86 thereby providing the attachment.

This exact procedure can be repeated with an initial step of inserting a hollow anchoring sleeve such as those depicted in FIGS. 4–6, and then having at the completion of the procedure the anchor means 105 inserted therein.

Therefore, there is provided a novel enhanced knotless suture anchor assembly which includes in a preferred embodiment, an anchor means as depicted in FIGS. 1, 2 or 3 and a free standing suture loop element as depicted in FIG. 7. Further, the assembly can include, if desired, a hollow anchoring sleeve as set forth in FIGS. 4–6.

In addition to the anchor assembly, there is depicted a method for the attachment of tissue to a bone mass utilizing the novel assembly.

In many situations throughout the discussion above, the terminology "secure attachment of tissue to bone mass" has been used. Such terminology refers to the attachment or reattachment of tissue to a bone mass by securely binding the tissue to the bone mass utilizing the novel knotless suture anchor assembly. The suture element can be made up of a known suture material, or it can be made of polymer materials, or can be formed of bioabsorbable material such as a polylactide polymer.

While a preferred embodiment of the invention is illustrated, it should be understood that the present disclosure is made by way of example and that variations to the structure shown and its use are possible within the scope of this disclosure without departing from the subject matter coming within the scope of the claims.

What is claimed is:

1. A knotless suture anchor assembly for attachment of tissue to a bone mass, said assembly comprising an anchor means having a snag means located therewith, and a free standing loop suture element comprising at least one suture element, wherein said snag means captures said free standing continuous loop suture element to draw said tissue into secure attachment with said bone mass.

2. A knotless suture anchor assembly as claimed in claim 1, wherein said snag means is a recess formed in said anchor means or an element attached to said anchor means to capture said free standing suture loop element and allow said tissue to be drawn to said bone mass.

3. A knotless suture anchor assembly as claimed in claim 1, further comprising a hollow anchoring sleeve for installation and attachment to said bone mass for receiving said anchor means.

4. A knotless suture anchor assembly as claimed in claim 3, wherein said hollow anchoring sleeve has a collar at a top section facilitating its attachment to said bone mass.

5. A method for the attachment of tissue to a bone mass utilizing said knotless suture anchor assembly as claimed in claim 1 comprising the steps of:

a) passing said free standing loop suture element to said tissue; and b) capturing a continuous loop of said free standing suture element with said snag means of said anchor means; and installing said anchor means into said bone mass for attachment of said tissue to said bone mass.

6. The method for the attachment of tissue to a bone mass utilizing said knotless suture anchor assembly as claimed in claim 3 comprising the steps of:

a) installing said hollow anchoring sleeve into said bone mass;

b) passing said free standing loop suture element to said tissue; and c) capturing a continuous loop of said free standing suture element with said snag means of said anchor means; and installing said anchor means into said hollow anchoring sleeve.

* * * * *